(12) United States Patent
Imling et al.

(10) Patent No.: US 6,203,499 B1
(45) Date of Patent: *Mar. 20, 2001

(54) MULTIPLE ANGLE NEEDLE GUIDE

(75) Inventors: Deborah K. Imling, Bellevue; Peter M. Pawluskiewicz, Seattle, both of WA (US)

(73) Assignee: ATL Ultrasound Inc., Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/166,486

(22) Filed: Oct. 5, 1998

(51) Int. Cl.⁷ ........................................ A61B 8/00
(52) U.S. Cl. ............................................ 600/461
(58) Field of Search ................... 600/461, 562, 600/567

(56) References Cited

U.S. PATENT DOCUMENTS

| | | | |
|---|---|---|---|
| 4,058,114 | * 11/1977 | Soldner | 600/461 |
| 4,608,989 | * 9/1986 | Drue | 600/461 |
| 4,742,829 | * 5/1988 | Law et al. | 600/461 |
| 4,838,506 | * 6/1989 | Cooper | 600/461 |
| 5,623,931 | * 4/1997 | Wung et al. | 600/461 |
| 5,752,962 | 5/1998 | D'Urso . | |
| 5,758,650 | 6/1998 | Miller et al. . | |

FOREIGN PATENT DOCUMENTS

| 29 42 405 | 4/1981 | (DE) . |
|---|---|---|
| 84 03034 | 8/1984 | (WO) . |

* cited by examiner

Primary Examiner—Francis J. Jaworski
(74) Attorney, Agent, or Firm—Edward A. Uhl

(57) ABSTRACT

A needle guide is provided for quick, easy, and consistent insertion of a needle, such as a biopsy needle, into the scan plane of an ultrasonic diagnostic imaging system probe at multiple angles. The needle guide of the present invention is preferably a one piece needle guide that provides the user with the ability to maneuver a needle into and within the tissue of a body being examined at various angles. The ability to maneuver a needle at multiple angles is obtained by insertion of a needle into a slot created within the body of the needle guide. The needle guide is configured to attach to a probe such that the needle will always be inserted into the scan plane of the probe regardless of the selected angle.

12 Claims, 3 Drawing Sheets

MULTIPLE ANGLE NEEDLE GUIDE

Figure 1:
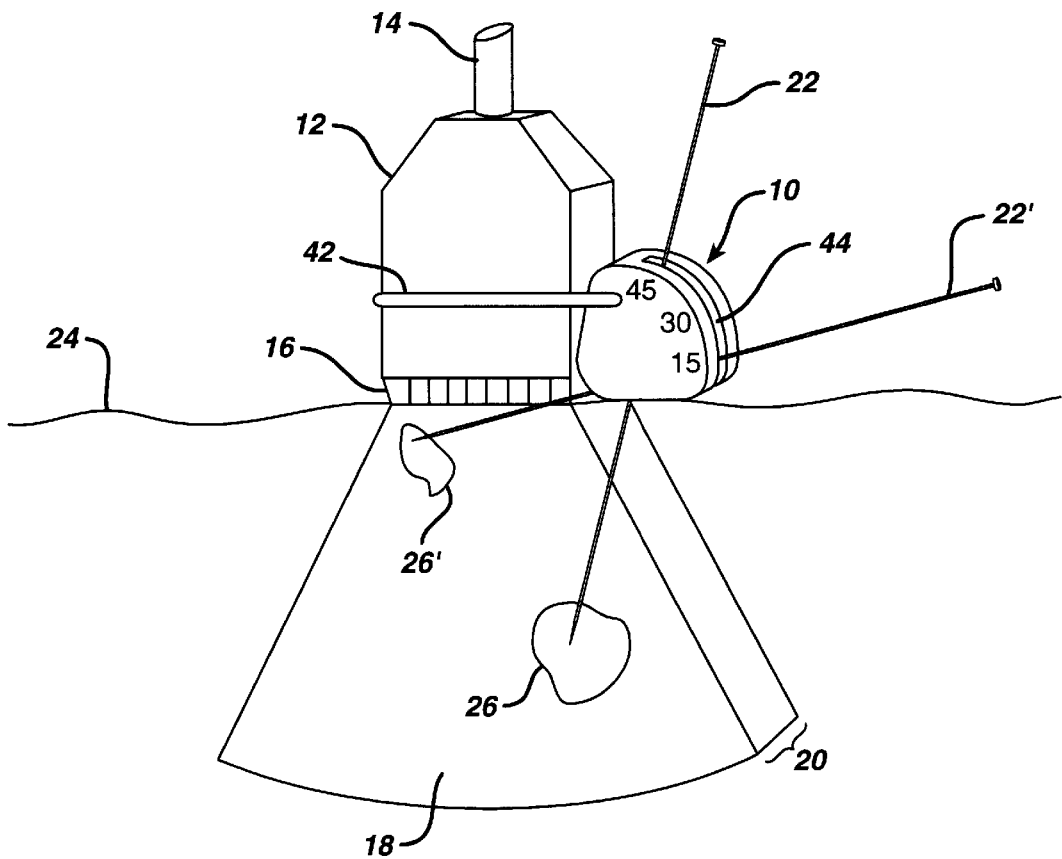

This invention relates to a needle guide, in particular, to a multiple angle needle guide that consistently guides a needle into a scan plane of an ultrasonic diagnostic imaging system probe.

Ultrasonic diagnostic imaging systems are in widespread use for performing ultrasonic imaging and measurements of the human body through the use of probes which may be placed internal or external to the body being measured. Such probes are used to view the internal structure of a body by creating a scan plane. The scan plane is produced from an array of transducers that transmit pulses or beams of energy into the body and receive returning pulses of energy as they are reflected from internal structures of the body. The scan plane is essentially the field of view inside the body being measured. The scan plane is displayed on the display of an imaging system and may have a variety of shapes. The most common scan planes are sector, rectangular (linear), or trapezoidal shaped, where the shape depends upon the type of transducer used in the probe.

Scan planes created by a one dimensional transducer array or a swept beam have two dimensions. For example, the first dimension is the area covered by the scan plane itself. The second dimension is the thickness or elevation dimension of the scan plane as it covers a certain area. Scan planes may be focused or shaped to obtain better resolution of a target or the region around the target (the "region of interest"). As a scan plane is focused, it is well known that the thickness or elevation dimension of the scan plane will become smaller. Focusing or shaping of a scan plan may be accomplished by using a lens or a contoured reflector, by using a curved array transducer, or by using a multi-element or phased array transducer in which the elements of the transducer are energized in a certain progressive pattern to create the desired shape of the scan plane.

Certain medical examinations, such as biopsies, benefit from the use of an imaging system. In such examinations, a needle, such as a biopsy needle, is inserted into a patients body for the purpose of extracting tissue samples, cellular materials, or fluids from a target, such as a cyst. The imaging system is used to view the region of interest, to detect the location of the needle while it is within the region of interest, and to provide feedback to the user so the needle can be better maneuvered.

In a typical biopsy examination the region of interest must first be located within the scan plane and displayed on the imaging system display. A user may then insert a needle, with or without a needle guide, into the body being examined. As the needle enters the scan plane of the probe, the energy pulses from the transducer array are reflected from the needle and returned to the transducer array. A display of the needle in relation to the region of interest will now be shown on the imaging system display. The user may continuously monitor the display to detect and maneuver the location of the needle in relation to the target within the region of interest. The needle, however, must be within the scan plane of the probe to be detected and displayed.

The insertion of a needle without a needle guide may be referred to as the freestyle technique. An advantage of the freestyle technique is the ability of the user to freely change the angle of the needle both before and after the needle has been inserted in the body being examined. The angle of the needle can be changed while it is inserted in the body being examined by backing the needle out of the body without removing the needle completely, re-adjusting the angle of the needle, and then applying a downward pressure on the needle to change its path to the newly selected angle.

The freestyle technique, however, has some drawbacks because it is difficult to insert the needle within the scan plane so the needle is detected by the transducer array. Even if the needle falls within the scan plan upon initial insertion, it is difficult to keep the needle completely within the scan plan during an examination. It is particularly difficult to keep the needle within the scan plane if the region of interest is at a greater depth within the body being examined because the thickness or elevation dimension of the scan plan will become smaller as the beam becomes focused at the target.

Each time an inserted needle fails to fall within the scan plane upon initial insertion or falls outside of the scan plane after needle insertion, the needle must be backed out fully or partially, and then re-inserted into the body until the needle is located within the scan plane. Such re-insertions may cause discomfort in the patient being examined and may also frustrate the user causing delay and further discomfort to the patient. Also, a high degree of skill and eye-hand coordination are required to properly maneuver the needle with the freestyle technique. For example, if the examination is an aspiration of fluids from a target such as a cyst, the target will typically shrink in size as the fluids are extracted. Since the needle must be continually relocated as the target shrinks, the required skill level increases as the size of the target decreases.

Needle guides have been used to resolve the difficulties associated with the freestyle technique, particularly the difficulty of inserting the needle within the scan plane such that the needle is detected by the transducer array. Existing needle guides attempt to resolve such difficulties by confining the needle to one pre-selected path of travel such that upon initial insertion, the needle will fall within the scan plane. Such needle guides, however, have not resolved the difficulty of keeping the needle completely within the scan plan because the needle may fall outside of the scan plane due to movement of the needle within the needle guide itself after it has been inserted. Moreover, such difficulties are amplified as the thickness or elevation dimension of the scan plane decreases. Existing needle guides have also eliminated advantages of the freestyle technique such as being able to select multiple angles of insertion and to freely maneuver and change angles of the needle once it has been inserted into the body being examined.

Fixed angle needle guides also make it difficult to reach certain target areas because a user is limited in needle movement. For example, in breast tissue biopsies, a target such as a cyst may be located close to the surface of the breast. In such cases, the needle must be inserted at a shallow angle such that it is almost parallel to the surface of the body being examined. The user may puncture a lung or even the heart of a patient during a breast biopsy if the needle is inserted at a steep angle, such as forty-five degrees. Since fixed angle needle guides typically provide insertion angles that are at a steep angle in relation to the surface of the body being examined, some fixed angle needle guides may increase the risk of injury in such examinations.

Moreover, existing needle guides are often bulky and cumbersome and present problems when a needle must be released from the probe in a quick and easy manner. When a needle is attached to a probe, or to a probe holding device, and the probe is firmly placed against the patient, a sudden movement by the patient may cause internal tissue damage from the needle if the needle is not immediately released from the probe. In an attempt to provide a quick and easy release of the needle, needle guides with quick release handles were provided to quickly remove the needle from the probe. Such devices, however, tend to be bulky, cumbersome, and difficult to operate. Thus, removal of the needle from the probe is not always quick and easy with existing needle guides.

Existing fixed angle needle guides that are designed to insert the needle into the scan plane do not always position the needle completely within the scan plane of the probe as designed. For example, if the dimensions of the needle guide pieces, the probe, or the needle itself are not constructed within tight manufacturing tolerance specifications, the needle guide can inaccurately position the needle outside of the scan plane and the needle will not be detected.

Multiple piece needle guides or bulky needle guides also present problems when the needle guide must be cleaned. If the needle guide has multiple pieces, some pieces may be disposable while other pieces may not be disposable. Since it is not always easy to distinguish non-disposable pieces from disposable pieces, expensive non-disposable pieces are often discarded with the disposable pieces. Also, if the needle guide is bulky there is typically a greater number of crevices that make cleaning difficult.

Needle guides are generally sized for one needle size, ranging from a large needle at 16 gauge to smaller needles at 22 gauge. Some needle guides provide a needle holding device that is designed for holding two different size needles. The limited capabilities of existing needle guides presents problems for users because the user must always have a wide range of needle guides or a wide range of needle holding devices available to accompany the large range of needles that may be required during different types of medical examinations.

Accordingly, it is desirable to have a needle guide that consistently guides a needle into the insertion point of the body being examined such that the needle always enters the scan plane, while also providing the benefits of mobility offered by the freestyle technique described above. Such a needle guide is preferably a one piece device that is easy to operate, easy to clean, can be used with a wide range of needle sizes, and can quickly and easily release a needle when required.

In accordance with the principles of the present invention, a one piece needle guide is provided that consistently guides a needle into the insertion point of the body being examined such that the needle always enters the scan plane. The needle guide of the present invention also provides the user with the ability to freely maneuver the needle at multiple angles before and after insertion of the needle into the body being examined, while keeping the needle within the scan plane such that it is detected. The needle guide of the present invention is easy to clean, easy to operate, can be used with a wide range of needle sizes, and allows for the quick and easy release of the needle from the needle guide if required.

Figure 2A:
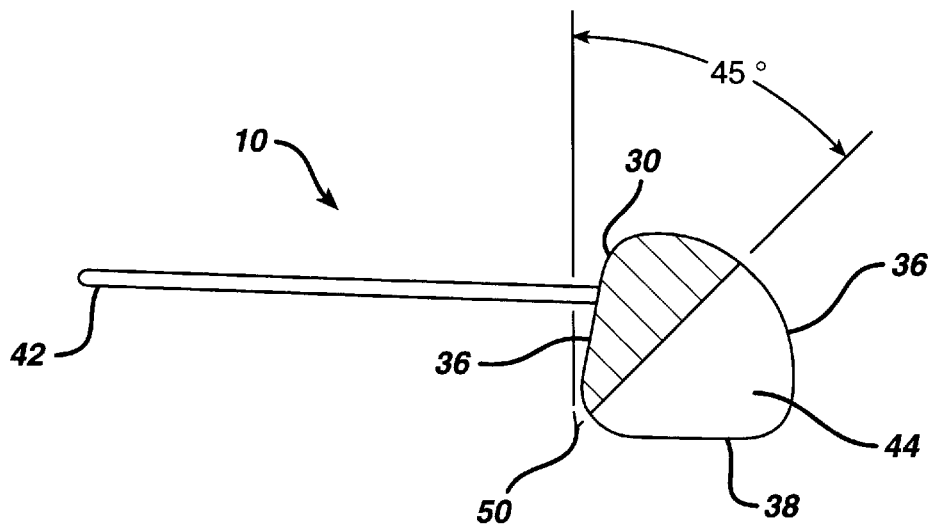
Figure 2B:
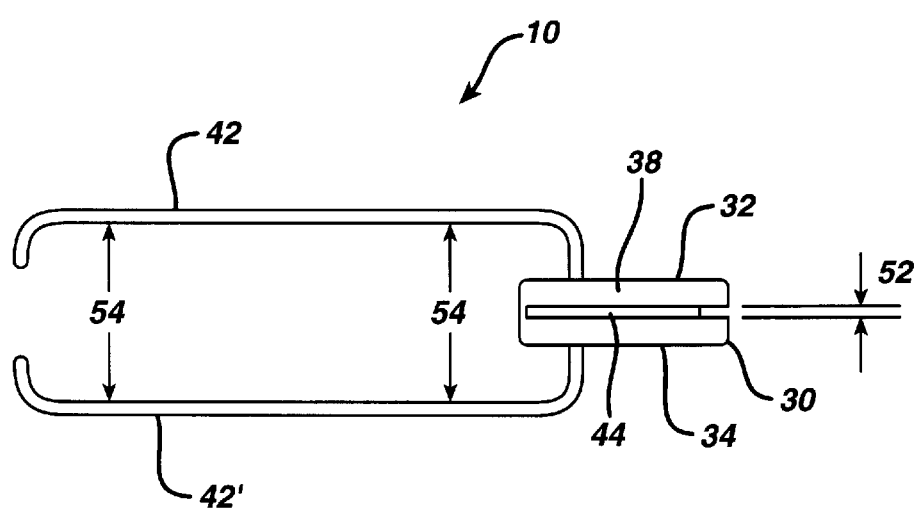
Figure 2C:
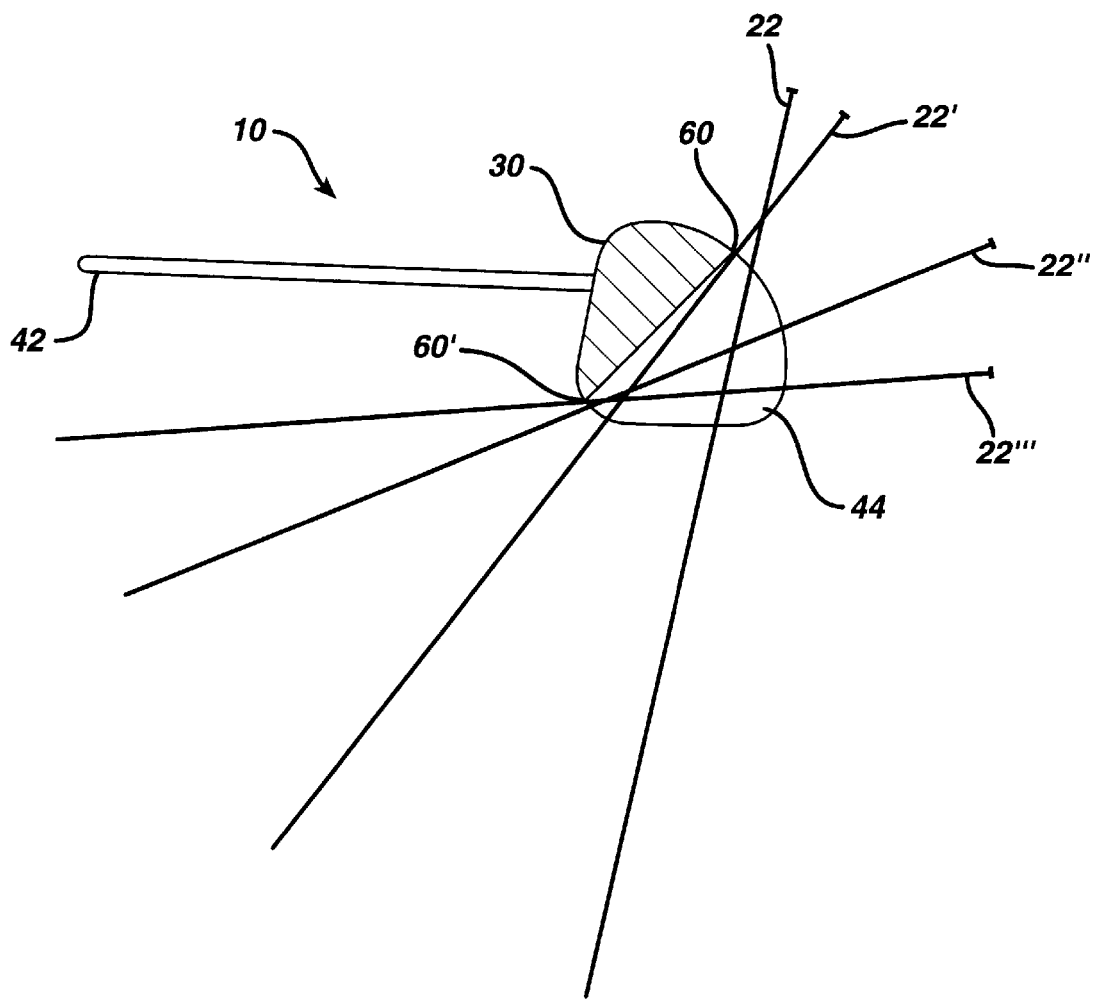

In the drawings:

FIG. 1 illustrates in perspective view a needle guide constructed in accordance with the principles of the present invention in use with an ultrasonic imaging probe; and FIGS. 2a–2c are plan views which illustrate the details of a needle guide constructed in accordance with the principles of the present invention.

Referring first to FIG. 1, a needle guide 10 constructed in accordance with the principles of the present invention is shown with ultrasonic imaging probe 12. Probe 12 is shown with cable 14, which electrically connects the probe to an ultrasonic diagnostic imaging system (not shown). Probe 12 includes a transducer array 16, which transmits ultrasonic beams in a scan plane 18. Scan plane 18 is shown as being trapezoidal shaped, having a thickness or elevation dimension 20. The present invention, however, may be used with other shapes of scan planes such as rectangular (linear) scan planes. Probe 12 is shown in contact with patient surface 24 scanning targets 26 and 26'.

Once target 26 is detected by scan plane 18, a needle 22, such as a biopsy needle, may be placed in slot 44 of needle guide 10. Prior to insertion of needle 22 into surface 24, the user may position needle 22 at any obtainable angle within slot 44. After needle 22 is positioned at the desired angle in slot 44, the user will apply a downward pressure to needle 22 such that needle 22 penetrates surface 24.

Needle guide 10 is secured to probe 12 by arms 42 and 42' (see FIG. 2b) such that slot 44 is aligned with elevation dimension 20 of scan plane 18. As the user inserts needle 22 into surface 24, needle 22 will enter scan plane 18 within elevation dimension 20. While needle 22 is within scan plane 18, transducer array 16 will detect the presence of needle 22 and send information back to the ultrasonic diagnostic imaging system (not shown), which will display the position of needle 22 within scan plan 18. Since needle 22 will enter scan plane 18 and elevation dimension 20 upon initial insertion, the user will not have to re-insert the needle. The user will now be able to better maneuver needle 22 by monitoring its location on the display. Once needle 22 reaches target 26, the user may perform the desired examination.

If the desired examination is the aspiration of fluids, target 26 may shrink in size as fluids are extracted. In such cases, it may be necessary to reposition needle 22 with respect to target 26 as it shrinks. If the user desires to reposition needle 22 the user can do so by pulling back on needle 22 such that needle 22 is slightly backed out of surface 24. The user may reposition needle 22 by changing the angle of needle 22 within slot 44 and redirecting needle 22 back into surface 24.

If the desired examination is a breast biopsy, it is preferable to insert the needle with little or no angle when the target is close to the surface being examined. FIG. 1 shows needle 22' inserted at a shallow angle in relation to probe 12 and surface 24 such that target 26' can be reached with little difficulty.

A wide range of insertion angles may be selected with needle guide 10. The desired angle may be selected prior to needle insertion by locating needle 22 at the desired angle within slot 44. As can be seen by the prior examples, needle guide 10 offers the benefits of consistently introducing needle 22 within the elevation dimension 20 of scan plane 18 at any selected angle, such that needle 22 is detected by transducer array 16. Needle guide 10 also provides the user with the ability to quickly and easily reposition needle 22 while it is inserted in surface 24 by changing the angle of needle 22 within slot 44. Moreover, needle 22 is not attached to needle guide 10; thus, if the patient being examined makes any sudden movements, needle 22 can be instantly released from needle guide 10 by lifting the probe away from surface 24.

Turning now to FIGS. 2a–2c, the details of a needle guide constructed in accordance with the principles of the present invention are shown. Needle guide 10 is comprised of body 30 for stabilizing a needle 22 while it is positioned within slot 44. Body 30 has two opposing sides 32 and 34, top side 36, and bottom side 38. Slot 44 is positioned in body 30 between opposing sides 32 and 34. Arms 42 and 42' are also shown attached to body 30.

FIG. 2a shows a side view of needle guide 10. A cross section of body 30 reveals that slot 44 creates a triangular shaped gap between opposing sides 32 and 34 and creates a partial opening between top side 36 and bottom side 38. Slot 44 is shown spanning a range of forty five degrees from theoretical corner 50, for inclination of the needle.

FIG. 2b shows a bottom view of needle guide 10. The bottom view of needle guide 10 shows that slot 44 is positioned within the center of body 30 leaving an opening at top side 36 and bottom side 38 to permit positioning of a needle at various angles. The width of slot 44, as depicted by arrow 52, may be sized to accommodate multiple needle sizes. Arms 42 and 42' are generally rigid but will flex enough to permit attachment to probe 12. Arms 42 and 42' may be slightly bowed to fit snugly around probe 12 as shown by arrows 54. Needle guide 10 is preferably a one piece design such that arms 42 and 42' are permanently attached to body 30; however, numerous attachment configurations will be readily apparent to those skilled in the art.

FIG. 2c is similar to FIG. 2a except that needles 22, 22', 22" and 22''' are shown positioned at various angles within slot 44. In any selected angle, needle 22 may freely move within slot 44 while it is inserted in the body being examined. Needle 22' is shown pivoting from point 60, while needles 22" and 22''' are shown pivoting from point 60'. The configuration of needle guide 10 permits the user to freely maneuver the needle over a range of insertion angles, while providing a stabilizing body for the needle that directs the needle into the scan plane and keeps the needle in the scan plane.

In a preferred embodiment of the present invention, body 30 and arms 42 and 42' are made from stainless steel. Markings may also be provided on either of opposing sides 32 or 34, top side 36, or bottom side 38 to provide an indication as to the angle of the needle, as shown in FIG. 1.

What is claimed is:

1. A needle guide for guiding a needle within a scan plane of an ultrasonic diagnostic imaging system probe comprising:

a body having two opposing sides;

a slot positioned between said opposing sides for guiding said needle within said scan plane at a plurality of angles, wherein said slot is sized to receive a plurality of needle sizes, wherein said slot comprises means for quickly releasing said needle from said needle guide; and attachment means for securing said body to said probe, wherein said attachment means offsets said body from transmission of said scan plane.

2. The needle guide of claim 1, wherein said slot encompasses a 45 degree range of angles.

3. The needle guide of claim 1, wherein said slot comprises means for freely maneuvering said needle at various angles while said needle is in said scan plane.

4. The needle guide of claim 1, wherein said attachment means is bowed to snuggly attach to said probe.

5. The needle guide of claim 1, wherein said attachment means is adapted to be removably secured to said probe.

6. The needle guide of claim 1, wherein said body has markings for indicating the angle of said needle within said needle guide.

7. The needle guide of claim 1, wherein said attachment means is permanently fastened to said body.

8. A needle guide for guiding a needle within a scan plane of an ultrasonic diagnostic imaging system probe comprising:

a body having two opposing sides;

a slot positioned between said opposing sides for guiding said needle within said scan plane at a plurality of angles, said slot being sized to fit a plurality of needle sizes, said slot comprising means for quickly releasing said needle from said slot, and said slot further comprising means for freely maneuvering said needle while said needle is in said scan plane; and attachment means for removably securing said body to said probe, wherein said attachment means offsets said body from transmission of said scan plane.

9. The needle guide of claim 8, wherein said slot encompasses a 45 degree range of angles.

10. The needle guide of claim 8, wherein said attachment means is bowed to snuggly attach to said probe.

11. The needle guide of claim 8, wherein said body has markings for indicating the angle of said needle within said needle guide.

12. The needle guide of claim 8, wherein said attachment means is permanently fastened to said body.

* * * * *